US009976160B2

(12) United States Patent
Kurihara et al.

(10) Patent No.: US 9,976,160 B2
(45) Date of Patent: May 22, 2018

(54) METHOD OF PRODUCING SUGAR LIQUID

(71) Applicant: Toray Industries, Inc., Tokyo (JP)

(72) Inventors: Hiroyuki Kurihara, Kamakura (JP); Hiroko Ishizuka, Kamakura (JP); Katsushige Yamada, Kamakura (JP)

(73) Assignee: Toray Industries, Inc. (JP)

( * ) Notice: Subject to any disclaimer, the term of this patent is extended or adjusted under 35 U.S.C. 154(b) by 0 days. days.

(21) Appl. No.: 14/903,642

(22) PCT Filed: Jul. 8, 2014

(86) PCT No.: PCT/JP2014/068115
§ 371 (c)(1),
(2) Date: Jan. 8, 2016

(87) PCT Pub. No.: WO2015/005307
PCT Pub. Date: Jan. 15, 2015

(65) Prior Publication Data
US 2016/0145651 A1 May 26, 2016

(30) Foreign Application Priority Data

Jul. 9, 2013 (JP) ................................ 2013-143403

(51) Int. Cl.
| | | |
|---|---|---|
| *C12P 7/14* | (2006.01) | |
| *C13B 50/00* | (2011.01) | |
| *C13B 30/02* | (2011.01) | |
| *C12P 19/02* | (2006.01) | |
| *C12P 19/14* | (2006.01) | |
| *C12N 1/22* | (2006.01) | |
| *C12P 7/10* | (2006.01) | |
| *C13B 20/00* | (2011.01) | |
| *C13B 30/00* | (2011.01) | |
| *C13K 1/04* | (2006.01) | |
| *C13K 5/00* | (2006.01) | |
| *C13K 13/00* | (2006.01) | |

(52) U.S. Cl.
CPC .................. *C12P 7/14* (2013.01); *C12N 1/22* (2013.01); *C12P 7/10* (2013.01); *C12P 19/02* (2013.01); *C12P 19/14* (2013.01); *C13B 20/002* (2013.01); *C13B 30/002* (2013.01); *C13B 50/00* (2013.01); *C13K 1/04* (2013.01); *C13K 5/00* (2013.01); *C13K 13/00* (2013.01); *C13K 13/002* (2013.01); *C12P 2203/00* (2013.01); *Y02E 50/16* (2013.01); *Y02E 50/17* (2013.01)

(58) Field of Classification Search
None
See application file for complete search history.

(56) References Cited

U.S. PATENT DOCUMENTS

| | | |
|---|---|---|
| 2006/0035355 A1 | 2/2006 | Ohara et al. |
| 2010/0267999 A1 | 10/2010 | Lau et al. |
| 2011/0250637 A1 | 10/2011 | Kurihara et al. |
| 2012/0196335 A1* | 8/2012 | Chatterjee ............... C12P 7/26 435/128 |
| 2014/0287461 A1 | 9/2014 | Kurihara et al. |

FOREIGN PATENT DOCUMENTS

| | | |
|---|---|---|
| JP | 11-506934 A | 6/1999 |
| JP | 3041380 B | 3/2000 |
| JP | 2001-095597 A | 4/2001 |
| JP | 2001-511418 A | 8/2001 |
| JP | 2003-212888 A | 7/2003 |
| JP | 2004-187650 A | 7/2004 |
| JP | 2005-229821 A | 9/2005 |
| JP | 2005-270056 A | 10/2005 |
| JP | 2008-161125 A | 7/2008 |
| JP | 2008-535664 A | 9/2008 |
| JP | 4770987 B | 7/2011 |
| JP | 2011-205987 | 10/2011 |
| WO | 96/40970 A1 | 12/1996 |
| WO | 99/06133 A1 | 2/1999 |
| WO | 2010/067785 A1 | 6/2010 |
| WO | 2011/044326 | 4/2011 |
| WO | WO 2012-036884 | * 3/2012 |
| WO | 2013/162478 | 10/2013 |

OTHER PUBLICATIONS

Whisstock et al. Quaterly Reviews of Biophysics, 2003, "Prediction of protein function from protein sequence and structure", 36(3): 307-340.*

Witkowski et al. Conversion of a beta-ketoacyl synthase to a malonyl decarboxylase by replacement of the active-site cysteine with glutamine, Biochemistry. Sep. 7, 1999;38(36)11643-50.*

Kisselev L., Polypeptide release factors in prokaryotes and eukaryotes: same function, different structure. Structure, 2002, vol. 10: 8-9.*

Ria Millati et al., "Effect of pH, time and temperature of overliming on detoxification of dilute-acid hydrolyzates for fermentation by *Saccharomyces cerevzsiae*," Process Biochemistry, vol. 38, 2002, pp. 515-522.

A. Aden et al., "Lignocellulosic Biomass to Ethanol Process Design and Economics Utilizing Co-Current Dilute Acid Prehydrolysis and Enzymatic Hydrolysis for Corn Stover," NREL Technical Report, Jun. 2002, NREL/TP-510-32438.

M.J. López et al., "Isolation of microorganisms for biological detoxification of lignocellulosic hydrolysates," Applied Biochemistry and Biotechnology, vol. 64, No. 1, 2004, pp. 125-131.

Nancy N. Nichols et al., "Bioabatement to Remove Inhibitors from Biomass-Derived Sugar Hydrolysates," Applied Biochemistry and Biotechnology, vol. 121-124, 2005, pp. 379-390.

(Continued)

*Primary Examiner* — Iqbal H Chowdhury
(74) *Attorney, Agent, or Firm* — DLA Piper LLP (US)

(57) ABSTRACT

A method of producing a sugar liquid from biomass includes decomposing a fermentation inhibitor contained in a sugar aqueous solution obtained from biomass with a microorganism incapable of utilizing glucose and/or xylose or a crude enzyme derived from the microorganism, wherein the fermentation inhibitor includes one or more compounds selected from the group consisting of courmaric acid, coumaramide, ferulic acid, ferulamide, vanillin, vanillic acid, acetovanillone, furfural, and 3-hydroxymethylfurfural.

7 Claims, 5 Drawing Sheets

(56) References Cited

OTHER PUBLICATIONS

Nancy N. Nichols et al., "Fungal metabolism of fermentation inhibitors present in corn stover dilute acid hydrolysate," Enzyme and Microbial Technology, vol. 42, No. 7, 2008, pp. 624-630.

Nancy N. Nichols et al., "Fermentation of bioenergy crops into ethanol using biological abatement for removal of inhibitors," Bioresource Technology, vol. 101, No. 19, 2010, pp. 7545-7550.

Partial Supplementary European Search Report dated Mar. 3, 2017, from corresponding European Application No. 14822714.3.

Juárez-Jimenez, B. et al., Metabolic Characterization of a Strain (BM90) of *Deljlia tsuruhatensis* Showing Highly Diversified Capacity to Degrade Low Molecular Weight Phenols, *Biodegradation*, 2010, vol. 21, pp. 475-489.

Plaggenborg, R. et al., "The Coenzyme A-Dependent, Non-β-Oxidation Pathway and Not Direct Deacetylation is the Major Route for Ferulic Acid Degradation in *Delftia acidovorans*," FEMS *Microbiology Letters*, Elsevier Science B.V., 2001, vol. 205, pp. 9-16.

Supplementary European Search Report dated May 12, 2017, of corresponding European Application No. 14822714.3.

Australian Examination Report dated Apr. 13, 2017, of corresponding Australian Application No. 2014288309.

Andrews, P., et al., "The Biosynthesis of Polysaccharides," Phytochemistry, vol. 4, No. 5, Sep. 1965, pp. 751-757.

\* cited by examiner

METHOD OF PRODUCING SUGAR LIQUID

TECHNICAL FIELD

This disclosure relates to a method of producing a sugar liquid from biomass.

BACKGROUND

The process of fermentation production of chemical substances using sugars as raw materials has been used to produce various industrial raw materials. Currently, as these sugars to be used as fermentation raw materials, those derived from food materials such as sugar cane, starch, and sugar beet are industrially used. However, in view of the fact that an increase in the price of food raw materials is expected due to future increases in world population, or in an ethical view of the fact that sugars as industrial materials may compete with sugars for food, it has been a future issue to construct a process of efficiently producing a sugar liquid from a renewable nonfood resource, that is, cellulose-containing biomass, or a process of using the obtained sugar liquid as a fermentation raw material to efficiently convert it into an industrial raw material.

As methods of producing a sugar liquid from cellulose-containing biomass, disclosed are a method of producing a sugar liquid by subjecting cellulose and hemicellulose to acid hydrolysis using concentrated sulfuric acid (Japanese Unexamined Patent Application Publication (Translation of PCT Application) No. 11-506934 or Japanese Unexamined Patent Application Publication No. 2005-229821) and a method of producing a sugar liquid by subjecting cellulose-containing biomass to hydrolysis treatment with dilute sulfuric acid and then further subjecting the resultant to treatment with an enzyme such as cellulase (A. Adel et al., "Lignocellulosic Biomass to Ethanol Process Design and Economics Utilizing Co-Current Dilute Acid Prehydrolysis and Enzymatic Hydrolysis for Corn Stover," NREL Technical Report (2002)). In addition, as methods using no acids, disclosed are a method of producing a sugar liquid by subjecting cellulose-containing biomass to hydrolysis using subcritical water at about 250 to 500° C. (Japanese Unexamined Patent Application Publication No. 2003-212888), a method of producing a sugar liquid by subjecting cellulose-containing biomass to subcritical water treatment and then further subjecting the resultant to treatment with an enzyme (Japanese Unexamined Patent Application Publication No. 2001-95597), and a method of producing a sugar liquid by subjecting cellulose-containing biomass to hydrolysis treatment with pressurized hot water at 240 to 280° C. and then further subjecting the resultant to treatment with an enzyme (Japanese Patent No. 3041380).

However, in the hydrolysis of the cellulose-containing biomass, decomposition reactions of the generated sugars such as glucose or xylose also progress concurrently with the decomposition of cellulose or hemicellulose components; and by-products including furan compounds such as furfural or hydroxymethylfurfural and organic acids such as formic acid, acetic acid, or levulinic acid are also generated, which has been problematic. In addition, because the cellulose-containing biomass contains lignin components, which are aromatic polymers, the lignin components are decomposed in the acid treatment step to concurrently generate, as by-products, aromatic compounds with low molecular weight such as phenol. Those compounds work in a inhibitory fashion in the fermentation step using microorganisms, cause inhibition of the microorganism proliferation, decrease in the yield of fermentation products, and are therefore referred to as fermentation inhibitors, which have been a big problem when the cellulose-containing biomass sugar liquid is used as a fermentation raw material.

As a method of removing these fermentation inhibitors in the sugar liquid production process, a method called over-liming has been disclosed (R. Millati et al., "Effect of pH, time and temperature of overliming on detoxification of dilute-acid hydrolyzates for fermentation by *Saccaromyces cerevisiase*," Process Biochemistry, 38, 515-522 (2002)). In that method, fermentation inhibitors such as furfural or HMF are removed along with a calcium sulfate component by keeping a cellulose or saccharification liquid after an acid treatment for a certain period of time while heating to around 60° C. in the neutralization step by lime addition. However, there has been a problem in that the over-liming was less effective in the removal of organic acids such as formic acid, acetic acid, or levulinic acid.

In addition, as another method of removing fermentation inhibitors, disclosed is a method of evaporating and removing fermentation inhibitors by blowing steam into a sugar liquid from cellulose-containing biomass (Japanese Unexamined Patent Application Publication No. 2004-187650). However, such a method of evaporation and removal depends on the boiling point of the fermentation inhibitor; and removal efficiency is low in particular for fermentation inhibitors with a low boiling point such as organic acids and a large amount of energy has to be placed for attaining a sufficient removal efficiency, which has been problematic.

Further, a method of removing fermentation inhibitors by ion exchange is also available (Japanese Unexamined Patent Application Publication (Translation of PCT Application) No. 2001-511418). However, the cost has been a problem. A method of adsorbing and removing fermentation inhibitors using wood-based carbides, that is, active carbon or the like is also available. However, there has been a problem in that what is to be removed is limited to hydrophobic compounds (Japanese Unexamined Patent Application Publication No. 2005-270056).

Further, a method of removing fermentation inhibitors as membrane permeate using a nanofiltration membrane or a reverse osmosis membrane has been invented. However, additional separation equipment and energy input for the removal are required, which has been problematic (Japanese Patent No. 4770987).

As mentioned above, fermentation inhibitors contained in a biomass-derived sugar liquid inhibit microbial growth and metabolic conversion and therefore an adsorption treatment, ion exchange, heat evaporation, nanofiltration membrane, or the like has been used to remove those fermentation inhibitors; but there has been a problem in that the cost for the treatment cost is high or removable fermentation inhibitors are limited to particular compounds.

Accordingly, it could be helpful to provide a method of producing a sugar liquid, comprising the step of comprehensively removing various fermentation inhibitors by a simple treatment at low cost.

SUMMARY

We found out that the concentration of fermentation inhibitors contained in a biomass-derived sugar liquid can be reduced by utilizing mechanisms of metabolism in particular microorganisms and the obtained sugar liquid can be utilized as a fermentation raw material.

We thus provide:

[1] A method of producing a sugar liquid from biomass, comprising the step of decomposing a fermentation inhibitor contained in a sugar aqueous solution obtained from biomass with a microorganism incapable of utilizing glucose and/or xylose or a crude enzyme derived from the microorganism, wherein the fermentation inhibitor comprises one or more compounds selected from the group consisting of coumaric acid, coumaramide, ferulic acid, ferulamide, vanillin, vanillic acid, acetovanillone, furfural, and 3-hydroxymethylfurfural.

[2] The method of producing a sugar liquid according to [1], wherein the microorganism incapable of utilizing glucose and/or xylose is a *Delftia* microorganism (*Delftia* sp.).

[3] The method of producing a sugar liquid according to [1] or [2], wherein the microorganism incapable of utilizing glucose and/or xylose comprises one or more types selected from the group consisting of *Delftia acidovorans*, *Delftia lacustris*, *Delftia tsuruhatensis*, and *Delftia litopenaei*.

[4] The method of producing a sugar liquid according to any one of [1] to [3], wherein the sugar aqueous solution is a sugar aqueous solution obtained by hydrolyzing cellulose-containing biomass.

[5] The method of producing a sugar liquid according to [4], wherein the method comprises the step of preparing the sugar aqueous solution by subjecting the cellulose-containing biomass to one or more treatments selected from the group consisting of an acid treatment, an alkali treatment, a hydrothermal treatment, and an enzyme treatment.

[6] The method of producing a sugar liquid according to any one of [1] to [3], wherein the sugar aqueous solution comprises blackstrap molasses.

[7] The method of producing a sugar liquid according to any one of [1] to [6], wherein the fermentation inhibitor decomposition treatment step is a treatment at a monosaccharide concentration of less than 100 g/L.

[8] The method of producing a sugar liquid according to any one of [1] to [7], wherein the fermentation inhibitor decomposition treatment step is a treatment at a pH ranging from 6 to 11.

[9] A method of producing a sugar liquid, comprising subjecting a sugar liquid obtained by the production method according to any one of [1] to [8] to membrane concentration and/or evaporation concentration to increase a sugar concentration.

[10] A method of producing a solid sugar, comprising subjecting a sugar liquid obtained by the method of producing a solid sugar according to any one of [1] to [8] to membrane concentration and/or evaporation concentration to obtain the solid sugar.

[11] A sugar liquid obtained by the method of producing a sugar liquid according to any one of [1] to [9].

[12] A solid sugar obtained by the method of producing a solid sugar according to [10].

[13] A sugar liquid or solid sugar derived from cellulose-containing biomass or blackstrap molasses, wherein the content of one or more types of free amino acids selected from the group consisting of serine, threonine, asparagine, aspartic acid, glutamine, glutamic acid, proline, phenyl alanine, lysine, and histidine, which are impurities, is below the limit of detection.

[14] A method of producing a chemical substance, comprising the steps of obtaining a sugar liquid by the method of producing a sugar liquid according to any one of [1] to [9], and culturing a microorganism using the obtained sugar liquid as a fermentation raw material to convert a sugar into the chemical substance.

[15] A method of producing a chemical substance, comprising the steps of obtaining a solid sugar by the method of producing a solid sugar according to [10], and culturing a microorganism using the obtained solid sugar as a fermentation raw material to covert a sugar into the chemical substance.

The obtained sugar liquid can be used as fermentation raw materials for microorganisms and can be utilized as raw materials for various chemical substances.

DETAILED DESCRIPTION

Figure 1:
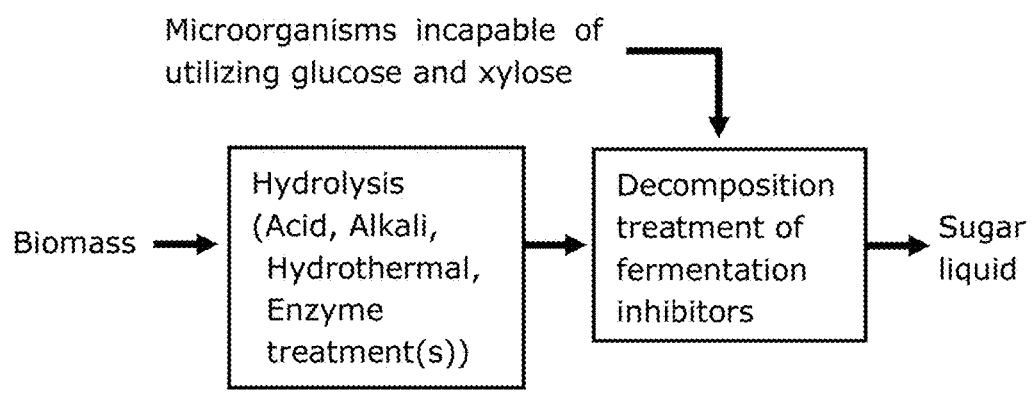
FIG. 1 is a flow diagram showing a procedure to carry out the method of producing a sugar liquid.
Figure 2:
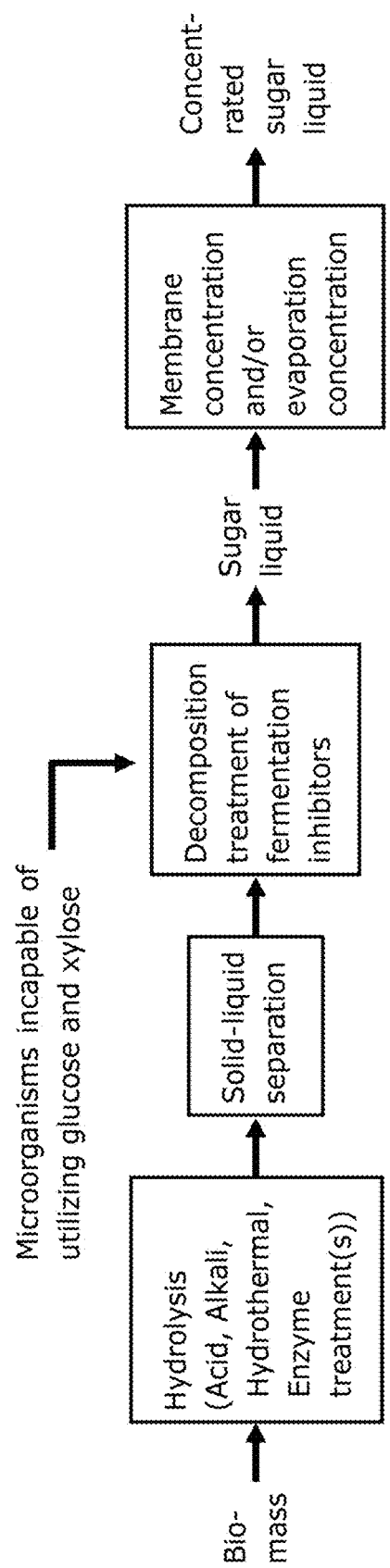
FIG. 2 is a flow diagram showing a preferred procedure to carry out the method of producing a sugar liquid.

We provide a method of producing a sugar liquid from biomass. The biomass is classified into sugar crops and grains containing sugars or polysaccharides and cellulose-containing biomass. Examples of the sugar crops and grains can include sugarcane, sweet potato, corn, sugar beet, cassava, rice, wheat, and soybean. Examples of the cellulose-containing biomass can include bagasse, corn stover, corncob, tree, tree bark, woody chip, waste building material, EFB (Empty fruits bunch), coconut husks, elephant grass, napier grass, Erianthus, switchgrass, wheat or barley straw, rice straw, giant reed, bamboo, coffee grounds, and tea leaves. That is, the sugar aqueous solution is a sugar liquid with such biomass as a raw material and a sugar aqueous solution obtained from the above-mentioned biomass through the step of extraction, concentration, hydrolysis, crystallization, or the like. Further, it refers to a sugar aqueous solution that contains at least sugar and a fermentation inhibitor described later.

Preferred examples of such a sugar aqueous solution include blackstrap molasses (molasses: mother liquor after sugar crystallization or a concentrate thereof) obtained in the step of producing sugars from sugar crops and grains and a sugar aqueous solution obtained by hydrolyzing cellulose-containing biomass.

Fermentation inhibitors are contained as impurities in a sugar aqueous solution. The fermentation inhibitor refers to a group of compounds derived from components of the above-mentioned biomass or generated by chemical conversion of the above-mentioned biomass, and that cause an action inhibitory to fermentation production by microorganisms. "Inhibitory" means that the presence of the fermentation inhibitor causes 1) delayed sugar consumption by microorganisms, 2) delayed proliferation of microorganisms, or 3) decreased production amount of fermentation products of microorganisms. With regard to 1) to 3), the presence of inhibition can be checked by comparison using a medium without the fermentation inhibitor as a reference standard. Further, to be specific, examples of the fermentation inhibitor can include furan-based compounds, aromatic compounds, and organic acids; and the reduction can be attained, in particular, by decomposing furan-based compounds and/or the aromatic compounds. The furan-based compound refers to a group of compounds having a furan backbone. Examples thereof include furfural and hydroxymethylfurfural; and the former is generated by conversion of xylose and the latter is generated by conversion of glucose. The aromatic compound is a compound having an aromatic ring; and examples thereof include vanillin, vanillic acid, syringic acid, coumaric acid, coumaramide, ferulic acid, and ferulamide.

The sugar aqueous solution contains, as fermentation inhibitors, one or more compounds selected from the group consisting of coumaric acid, coumaramide, ferulic acid, ferulamide, vanillin, vanillic acid, acetovanillone, furfural, and 3-hydroxymethylfurfural. When it comes to inclusion of those fermentation inhibitors in the sugar aqueous solution, a standard sample of the above-mentioned fermentation inhibitor can be separated by reversed phase chromatography (HPLC) to determine whether or not the corresponding fermentation inhibitor is contained in a sugar liquid based on retention time in a particular separation condition. In the reversed phase chromatography, the absorbance of an eluted solution at each retention time can be measured at 180 to 400 nm to obtain a chromatogram. In addition, a calibration curve can be prepared in advance by using standard samples of the fermentation inhibitor; and the concentration of the fermentation inhibitor in the sugar liquid can be determined by a corresponding peak area or peak height in the sugar liquid. Such an analysis may be carried out by concentrating or diluting the sugar liquid according to an analytical technique or device employed.

It is to be noted that the expression "one or more types of fermentation inhibitors selected from the group consisting of coumaric acid, coumaramide, ferulic acid, ferulamide, vanillin, vanillic acid, acetovanillone, furfural, and 3-hydroxymethylfurfural are contained in a sugar aqueous solution" means that these substances are contained in a detectable range in the sugar aqueous solution, and preferably contained at 1 mg/mL or more, more preferably at 10 mg/mL or more, and still more preferably at 100 mg/L or more. In addition, more than one of those fermentation inhibitors may be contained in the method of producing a sugar liquid; and two or more types, three or more types, or four or more types of those fermentation inhibitors may be contained.

At least sugars are contained in a sugar aqueous solution. Sugars refer to components dissolved in water among monosaccharides and polysaccharides and at least include monosaccharides composed of one of such sugars, disaccharides, or trisaccharides. Specific examples of the sugar can include glucose, xylose, arabinose, xylitol, arabitol, sucrose, fructose, lactose, galactose, mannose, cellobiose, cellotriose, xylobiose, xylotriose, maltose, and trehalose. The sugar concentration in the sugar aqueous solution is 0.01 g/L or more, preferably 0.1 g/L or more, still more preferably 1 g/L or more, and most preferably 10 g/L or more; and at least one type of the above-mentioned sugars is contained.

In addition to the above-mentioned fermentation inhibitor and sugar, inorganic salts, organic acids, amino acids, vitamins, and the like are further contained in a sugar aqueous solution. Examples of the inorganic salt include potassium salts, calcium salts, sodium salts, and magnesium salts. Examples of the organic acid include lactic acid, citric acid, acetic acid, formic acid, malic acid, and succinic acid. Examples of the amino acid include glutamine, glutamic acid, asparagine, aspartic acid, glycine, alanine, phenyl alanine, tyrosine, tryptophan, arginine, methionine, cysteine, histidine, leucine, isoleucine, lysine, proline, serine, threonine, and valine.

When biomass is cellulose-containing biomass, a sugar aqueous solution is obtained by carrying out hydrolysis of the cellulose-containing biomass in one or more treatments selected from the group of an acid treatment, an alkali treatment, a hydrothermal treatment, and an enzyme treatment. The hydrolysis is a treatment of hydrolyzing polysaccharides such as cellulose or hemicellulose that are contained in the cellulose-containing biomass into monosaccharides or oligosaccharides; and hydrolysates contain fermentation inhibitors in addition to these monosaccharides or oligosaccharides.

An acid treatment is carried out by adding an acid such as sulfuric acid, acetic acid, hydrochloric acid, or phosphoric acid to the biomass. Further, a hydrothermal treatment may be carried out in the acid treatment. In a sulfuric acid treatment, the concentration of sulfuric acid is preferably 0.1 to 15% by weight and more preferably 0.5 to 5% by weight. The reaction temperature can be 100 to 300° C. and preferably 120 to 250° C. The reaction time can be one second to 60 minutes. The number of times of the treatment is not particularly restricted and the above-mentioned treatment need only to be carried out once or more. In particular, when the above treatment is carried out twice or more, the first treatment and the second or later treatment may be carried out in different conditions.

An alkali treatment is carried out by adding an alkali such as ammonia, sodium hydroxide, potassium hydroxide to biomass. Further, a hydrothermal treatment may be carried out in the alkali treatment. An ammonia treatment is performed in accordance with a method described Japanese Patent Application Laid-Open Publication No. 2008-161125 or Japanese Patent Application Laid-Open Publication No. 2008-535664. For example, with regard to the ammonia concentration employed, ammonia is added in a range of 0.1 to 15% by weight based on the biomass. The treatment is carried out at 4 to 200° C. and preferably 90 to 150° C. The ammonia to be added may be either in a liquid state or in a gaseous state. Further, the form to be added may be pure ammonia or the form of aqueous ammonia solution. The number of times of the treatment is not particularly restricted and the above-mentioned treatment need only to be carried out once or more. In particular, when the above treatment is carried out twice or more, the first treatment and the second or later treatment may be carried out in different conditions.

A hydrothermal treatment is a method of treating cellulose-containing biomass by adding water alone, without adding any of acids and alkalis, followed by heating. In a hydrothermal treatment, water is added such that the biomass is at 0.1 to 50% by weight and the resultant is then treated at a temperature of 100 to 400° C. for one second to 60 minutes. The hydrolysis of cellulose takes place by treating the biomass in such a temperature condition. The number of times of the treatment is not particularly restricted and the treatment need only to be carried out once or more. In particular, when the above treatment is carried out twice or more, the first treatment and the second or later treatment may be carried out in different conditions.

As for an enzyme treatment, a hydrolysis treatment is carried out by adding a saccharification enzyme to the cellulose-containing biomass. The pH of the hydrolysis by the saccharification enzyme is preferably 3 to 9, more preferably 4 to 5.5, and still more preferably 5. For pH adjustment, an acid or alkali can be added to adjust to a desired pH. In addition, a buffer may be used as appropriate. In the enzyme treatment, to promote contact of the cellulose with the enzyme or to make the sugar concentration of hydrolysate uniform, mixing with stirring is preferred. With regard to the solid concentration of the cellulose, water is added to be preferably 1 to 25% by weight and more preferably 5 to 20% by weight.

As the saccharification enzyme, cellulases derived from filamentaous fungi can be preferably used. Examples of the filamentous fungus include the genus *Trichoderma*, the genus *Aspergillus*, the genus *Cellulomonas*, the genus *Clostridium*, the genus *Streptomyces*, the genus *Humicola*, the genus *Acremonium*, the genus *Irpex*, the genus *Mucor*, the genus *Talaromyces*, the genus *Phanerochaete*, white rot fungi, and brown rot fungi. Of these cellulases derived from filamentaous fungi, cellulases derived from the genus *Trichoderma* with a high cellulolytic activity are preferably used.

The cellulase derived from the genus *Trichoderma* is an enzyme composition with a cellulase derived from *Trichoderma* microorganisms as a major component. The *Trichoderma* microorganism is not particularly restricted. *Trichoderma reesei* is preferred and specific examples thereof can include *Trichoderma reesei* QM9414, *Trichoderma reesei* QM9123, *Trichoderma reesei* Rut C-30, *Trichoderma reesei* PC3-7, *Trichoderma reesei* CL-847, *Trichoderma reesei* MCG77, *Trichoderma reesei* MCG80, and *Trichoderma viride* QM9123. Further, mutant strains may also be used, which strains are obtained by subjecting the above-mentioned microorganism derived from the genus *Trichoderma* to mutagenesis by a mutagen or irradiation with UV and have improved cellulase productivity.

The cellulase derived from the genus *Trichoderma* is an enzyme composition that contains plural enzyme components including cellobiohydrolase, endoglucanase, exoglucanase, β-glucosidase, xylanase, and xylosidase and has an activity of hydrolyzing cellulose for saccharification. The cellulase derived from *Trichoderma* can perform an efficient hydrolysis of cellulose by concert effects or complementary effects of plural enzyme components in the decomposition of cellulose. In particular, the cellulase used preferably contains *Trichoderma*-derived cellobiohydrolase and xylanase.

Cellobiohydrolase is a general term for cellulases characterized by hydrolyzing cellulose from the terminal portion. The group of enzymes belonging to cellobiohydrolase is described as the EC number: EC3.2.1.91.

Endoglucanase is a general term for cellulases characterized by hydrolyzing cellulose molecular chains from their middle portion. The group of enzymes belonging to exoglucanase is described as the EC numbers: EC3.2.1.4, EC3.2.1.6, EC3.2.1.39, and EC3.2.1.73.

Exoglucanase is a general term for cellulases characterized by hydrolyzing cellulose molecular chains from their termini. The group of enzymes belonging to exoglucanase is described as the EC numbers: EC3.2.1.74 and EC3.2.1.58.

β-glucosidase is a general term for cellulases characterized by acting on cello oligosaccharides or cellobiose. The group of enzymes belonging to β-glucosidase is described as the EC number: EC3.2.1.21.

Xylanase is a general term for cellulases characterized by acting on hemicellulose or, in particular, xylan. The group of enzymes belonging to xylanase is described as the EC number: EC3.2.1.8.

Xylosidase is a general term for cellulases characterized by acting on xylooligosaccharides. The group of enzymes belonging to xylosidase is described as the EC number: EC3.2.1.37.

As the cellulase derived from *Trichoderma*, crude enzymes are preferably used. The crude enzyme is derived from the supernatant of culture, wherein the microorganism of the genus *Trichoderma* is cultured in the medium for any period of time, which medium is prepared such that the microorganism produces cellulase. Medium components used are not particularly restricted and a media with cellulose being added can be generally used to promote production of the cellulase. Then, as the crude enzyme, a culture liquid as is or the supernatant of the culture obtained only by removing *Trichoderma* bacterial cells is preferably used.

A weight ratio of each enzyme component in the crude enzyme is not particularly restricted. For example, a culture liquid derived from *Trichoderma reesei* contains 50 to 95% by weight cellobiohydrolase and the remaining components include endoglucanase, β-glucosidase, and the like. Further, the microorganism of the genus *Trichoderma* produces a strong cellulase component in a culture liquid. When it comes to β-glucosidase, because it retains β-glucosidase intracellularly or on the cell surface layer, the β-glucosidase activity is low in the culture liquid. Thus, β-glucosidase from different species or the same species may be further added to the crude enzyme. As the β-glucosidase from different species, β-glucosidase derived from the genus *Aspergillus* can be preferably used. Examples of the β-glucosidase derived from the genus *Aspergillus* include Novozyme 188 which is commercially available from Novozymes A/S. As a method of adding the β-glucosidase from different species or the same species to the crude enzyme, what may be also employed is a method comprising introducing a gene to the microorganism of the genus *Trichoderma*, culturing the genetically-modified microorganism of the genus *Trichoderma* to produce β-glucosidase in a culture liquid, and isolating the culture liquid.

It is preferred that two or more of the above-mentioned acid treatment, alkali treatment, hydrothermal treatment, and enzyme treatment be combined as appropriate; and it is more preferred that the enzyme treatment is further carried out to the cellulose-containing biomass that has been subjected to the acid treatment, the alkali treatment, or the hydrothermal treatment.

The fermentation inhibitor contained in the above-mentioned sugar aqueous solution is subjected to a decomposition treatment by a microorganism incapable of utilizing glucose and/or xylose and preferably by a microorganism incapable of utilizing glucose and xylose. The decomposition treatment of fermentation inhibitors is to involve a change in the chemical structure of the fermentation inhibitor by actions of a microorganism or an enzyme and to reduce microorganism toxicity by lowering the molecular weight of the fermentation inhibitor or by hydroxylating the fermentation inhibitor. The microorganism incapable of utilizing glucose and/or xylose or a crude enzyme derived from such a microorganism is used in the decomposition treatment of the fermentation inhibitor. This allows a wide range of the fermentation inhibitors to be efficiently decomposed and removed.

The microorganism incapable of utilizing glucose and/or xylose is a microorganism characterized by not substantially consuming xylose and/or glucose as carbon sources in a medium in which such a microorganism grows under culture conditions (optimum pH, optimum temperature, and optimum aeration condition). In addition, *Pseudomonas aeruginosa* which is known as an obligate aerobe, for example, utilizes glucose and/or xylose under anaerobic conditions and consumes glucose and/or xylose under aerobic conditions. Such a microorganism that does not utilize glucose and/or xylose depending on the condition is also included in what is referred to as the "microorganism incapable of utilizing glucose and/or xylose." It is to be noted that microorganisms that have lost the capability of utilizing glucose and/or xylose by gene recombination or by introducing gene mutation may also be used.

Examples of microorganisms incapable of utilizing glucose and/or xylose, which microorganisms can preferably be used can include microorganisms belonging to the genus *Delftia* (*Delftia* sp.), the genus *Comamonas* (*Comamonas* sp.), the genus *Derxomyces* (*Derxomyces* sp.), and the genus *Fellomyces* (*Fellomyces* sp.). Of those, *Delftia* microorganisms which have an excellent ability to decompose fermentation inhibitors are more preferred.

Examples of *Delftia* microorganisms can include *Delftia acidovorans, Delftia lacustris, Delftia tsuruhatensis*, and *Delftia litopenaei*.

It is to be noted that, as for the identification of *Delftia* microorganism, when the 16S rDNA base sequence of a microorganism to be identified is determined and compared to the 16S rDNA base sequence of *Delftia lacustris* 322 strain (Accession No. EU888308), if the sequence identity is 93% more, the microorganism can be identified to be the genus *Delftia*.

As the microorganism identified by the above-mentioned particular method, there are some microorganisms that are not assigned to the genus *Delftia* and have a different genus name. Those microorganisms are to be included in the *Delftia* microorganism and can be used in the method of producing a sugar liquid as long as they are characterized by not utilizing glucose and/or xylose and further characterized by decomposing the fermentation inhibitor. Specific examples of the genus name of microorganisms that may be included as microorganisms having 93% or more identity to the above-mentioned 16S RNA sequence and are characterized by decomposing the fermentation inhibitor include the genus *Comamonas*, the genus *Acidovorax*, the genus *Giesbergeria*, the genus *Simpliciriera*, the genus *Alicychphilus*, the genus *Diaphorobacter*, the genus *Tepidecella*, the genus *Xenophilus*, and the genus *Brachymonas*. All of these are microorganisms related closely to the genus *Delftia* and may be able to be used.

Further, a crude enzyme derived from a microorganism incapable of utilizing glucose and/or xylose refers to an enzyme component derived from the above-mentioned microorganism and containing two or more types of enzymatic components. Such a crude enzyme can be prepared by culturing the microorganism incapable of utilizing glucose and xylose in an appropriate medium and extracting a rough enzyme liquid from the cultured bacterial cells. The crude enzyme can also be produced as a heterogeneous recombinant protein by isolating a gene of the microorganism incapable of utilizing glucose and/or xylose and introducing the gene into an appropriate host to express the gene. Preferred is one obtained by culturing the microorganism incapable of utilizing glucose and/or xylose and extracting the enzyme from this microorganism. It is preferred to be one that does not undergo any particular purification operation. The crude enzyme contains two or more types of enzymatic components and is therefore able to decompose plural fermentation inhibitors all at once into compounds with reduced inhibitory activities.

A decomposition treatment of fermentation inhibitors is carried out by mixing the above-mentioned sugar aqueous solution containing the fermentation inhibitor with the above-mentioned microorganism or the above-mentioned crude enzyme derived from the microorganism and incubating the mixture under a condition of optimum growth temperature or optimum growth pH of the above-mentioned microorganism. A specific temperature condition is preferably 20 to 40° C. and more preferably 25° C. to 32° C. In addition, the pH condition is preferably 6.5 to 10 and more preferably 7 to 8.5.

Fermentation inhibitors to be decomposed are one type or more types, preferably two or more types, more preferably three or more types, and still more preferably four or more types selected from the group of coumaric acid, coumaramide, ferulic acid, ferulamide, vanillin, vanillic acid, acetovanillone, furfural, and 3-hydroxymethylfurfural.

Solids contained in a sugar solution may be removed in advance by solid-liquid separation. A method of solid-liquid separation is not particularly restricted and is preferably centrifugation such as a screw decanter and membrane separation by filter pressing, microfiltration membrane (microfiltration), or the like with membrane separation being more preferred.

The sugar aqueous solution may also be one subjected to ultrafiltration membrane (UF membrane: Ultrafultration) treatment. A method of ultrafiltration membrane treatment is not particularly restricted. As for the ultrafiltration membrane used, an ultrafiltration membrane with a molecular weight cut off of 500 to 200,000 Da and preferably 10,000 to 50,000 Da can be used. In particular, when an enzyme used in the hydrolysis of cellulose-containing biomass is contained in the sugar aqueous solution, the enzyme used in the hydrolysis can be separated and collected by using an ultrafiltration membrane with a smaller molecular weight cut off than the molecular weight of the enzyme.

With regard to the material of the ultrafiltration membrane, a membrane made of a material such as polyether sulfone (PES), polyvinylidene difluoride (PVDF), or regenerated cellulose can be used. As for the form of the ultrafiltration membrane, a tubular system, a spiral element, a flat sheet membrane, or the like can be preferably used. Examples of the ultrafiltration membrane filtration include a cross flow system or a dead end filtration system; and the cross flow filtration system is preferred in terms of the membrane fouling or flux.

The microorganism incapable of utilizing glucose and/or xylose or the crude enzyme derived from such a microorganism may be separated and collected from the sugar liquid after the decomposition treatment of the fermentation inhibitor to be reused. The above-mentioned separation and collection can be carried out by selecting as appropriate from or combining centrifugation, microfiltration membrane, ultrafiltration membrane, and the like. It is to be noted that the above-mentioned microorganism or the crude enzyme derived from the above-mentioned microorganism may be immobilized in advance on resins, gels, sponges, supports, or the like. Immobilization facilitates the separation and reuse of the microorganism and crude enzyme component from the sugar liquid and therefore is preferred. In particular, in the immobilization of the microorganism, cellulose sponges are preferred, which sponges have an excellent adherence property for the microorganism that is incapable of utilizing glucose and/or xylose.

The obtained sugar liquid is preferably subjected to the step of membrane concentration and/or evaporation concentration to increase the concentration of sugars. The increased concentration of sugars allows the obtained sugar liquid to be preferably used as a raw material in the production of chemical substances and, at the same time, leads to stability in storage and reduction of transportation costs; and is therefore preferred.

The membrane concentration is preferably concentration by a nanofiltration membrane and/or reverse osmosis membrane. Further, by filtration through the nanofiltration membrane and/or the reverse osmosis membrane which is a method described in WO 2010/067785, as a preferred example of membrane concentration, a concentrated sugar liquid in which the sugar component is concentrated can be obtained as a retentate.

The nanofiltration membrane is a membrane also called a nanofilter (nanofiltration membrane, NF membrane) and is in general defined as a "membrane permeating monovalent ions whereas blocking divalent ions." It is a membrane that is thought to have microvoids of about several nanometers and mainly used to block fine particles or molecules, ions, salts, or the like in water.

The reverse osmosis membrane is also called an RO membrane and is in general defined as a "membrane having a function of removing salts including monovalent ions." The membrane is a membrane thought to have ultramicrovoids ranging from about several angstroms to several nanometers and mainly used to remove ion components, for example, in desalination of sea water or production of ultrapure water.

Examples of materials of the nanofiltration membrane and/or the reverse osmosis membrane include composite membranes with a cellulose acetate-based polymer as a functional layer (hereinafter referred to as cellulose acetate-based reverse osmosis membranes) and composite membranes with polyamide as a functional layer (hereinafter referred to as polyamide-based reverse osmosis membranes). Examples of the cellulose acetate-based polymer include ones that uses solely organic acid esters of cellulose such as cellulose acetate, cellulose diacetate, cellulose triacetate, cellulose propionate, or cellulose butyrate; or a mixture of these; and a mixed ester. Examples of polyamide include linear polymers and cross-linked polymers with aliphatic and/or aromatic diamines as a monomer. Further, the membrane is not limited to a membrane composed of one type of the above-mentioned materials; and membranes containing plural membrane materials may also be used.

As the nanofiltration membrane, a spiral-type membrane element is preferably used. Specific examples of a preferred nanofiltration membrane element include GEsepa manufactured by GE Osmonics, which is a cellulose acetate-based nanofiltration membrane element; NF99 or NF99HF manufactured by Alfa Laval, which is a nanofiltration membrane element with polyamide as a functional layer; NF-45, NF-90, NF-200, NF-270, or NF-400 manufactured by Filmtec, which is a nanofiltration membrane element with cross-linked piperazine polyamide as a functional layer; and SU-210, SU-220, SU-600, or SU-610 manufactured by Toray Industries, Inc. which is a nanofiltration membrane element containing a nanofiltration membrane UTC60 manufactured by the same company with cross-linked piperazine polyamide as a major component. More preferred is NF99 or NF99HF; NF-45, NF-90, NF-200, or NF-400; or SU-210, SU-220, SU-600, or SU-610; and still more preferred is SU-210, SU-220, SU-600, or SU-610.

Specific examples of the reverse osmosis membrane include, in addition to ultra low pressure types SUL-G10 and SUL-G20, and low pressure types SU-710, SU-720, SU-720F, SU710L, SU-720L, SU-720LF, SU-720R, SU-710P, and SU-720P, which are polyamide-based reverse osmosis membrane modules manufactured by Toray Industries, Inc.; high pressure types SU-810, SU-820, SU-820L, and SU-820FA, which contain UTC80 as a reverse osmosis membrane; cellulose acetate-based reverse osmosis membranes SC-L100R, SC-L200R, SC-1100, SC1200, SC-2100, SC-2200, SC-3100, SC-3200, SC-8100, and SC-8200, which are manufactured by the same company; NTR-759HR, NTR-729HF, NTR-70SWC, ES10-D, ES20-D, ES20-U, ES15-D, ES15-U, and LF10-D, which are manufactured by Denko Corporation; RO98pHt, R099, HR98PP, and CE4040C-30D, which are manufactured by Alfa Laval; GE Sepa manufactured by GE; BW30-4040, TW30-4040, XLE-4040, LP-4040, LE-4040, SW30-4040, and SW30HRLE-4040, which are manufactured by Filmtec; TFC-HR and TFC-ULP, which are manufactured by KOCH; and ACM-1, ACM-2, and ACM-4, which are manufactured by TRISEP.

The obtained sugar liquid has an advantage in that the nanofiltration membrane and/or reverse osmosis membrane are more easily applicable compared to a conventional sugar liquid for which the fermentation inhibitor decomposition treatment is not carried out. This is presumably associated with reduction of the fermentation inhibitor in the sugar liquid; but detailed factors are unknown.

The evaporation concentration is a technique of increasing the concentration of the sugar liquid by putting the sugar liquid into a heated and/or reduced pressure state to vaporize and remove moisture in the sugar liquid. Examples of a commonly-used apparatus can include an evaporator, a flash evaporator, a multiple-effect evaporator, spray drying, and freeze drying.

The obtained sugar liquid contains monosaccharides or polysaccharides that have been contained in the sugar aqueous solution. Glucose, xylose, arabinose, mannose, sucrose, cellobiose, lactose, xylobiose, xylotriose, and the like are contained. As for a method of analyzing these sugar components in the sugar liquid, quantification can be performed by comparing to standard samples by HPLC.

The sugar liquid may be turned into a solid sugar by carrying out membrane concentration and/or evaporation concentration. The solid sugar refers to a sugar in a form of solid obtained by removing moisture in the sugar liquid to make the content of moisture less than 10% or preferably less than 5%. Making the solid sugar can reduce moisture or water activity in the sugar to decrease microorganism microbial contamination and further can reduce the cost of transportation of the sugar, which are advantageous. In addition, the solid sugar obtained from the sugar liquid obtained by the method of producing a sugar liquid is characterized by having a low hygroscopicity. Because the low hygroscopicity leads to less quality change during storage and/or transportation, the solid sugar can be stably used as an industrial raw material, which is advantageous in practice.

The sugar liquid or the solid sugar is characterized in that the content of one or more types of free amino acids selected from the group consisting of serine, threonine, asparagine, aspartic acid, glutamine, glutamic acid, proline, phenyl alanine, lysine, and histidine, which are impurities, is below the limit of detection. This is believed to be because fermentation inhibitors are decomposed by the microorganism incapable of utilizing glucose and/or xylose or the crude enzyme derived from such a microorganism and, as a result, a very small amount of free amino acids contained in a sugar aqueous solution is used for microbial proliferation and/or metabolism. On the other hand, amino acids contained in a peptide or polypeptide state are characterized by remaining in some amount in a sugar liquid or a solid sugar. From this, when the microorganism is propagated using the sugar liquid or the solid sugar as a fermentation raw material, the amino acids in a peptide or polypeptide state can be used as nutrient sources for microbial proliferation.

As for quantification of free amino acids contained in the sugar liquid or the solid sugar, measurement is preferably carried out by ninhydrin method using a commercially available amino acid analyzer. In addition, when the analysis of free amino acids is carried out, separation quantification by an amino acid analyzer can be carried out using 25 µL of a sample solution prepared by adding 250 µL of 2% sulfosalicylic acid to about 2 mg of a solid sugar or a solid sugar prepared by drying a sugar liquid, and stirring the resulting mixture, followed by ultrasonication for 10 minutes to prepare the sample solution for measurement. As for the amino acid analyzer, one manufactured by Hitachi, Ltd. is preferred and Amino Acid Analyzer L8800A is most preferred.

In particular with regard to the solid sugar, when the content of one or more types of free amino acids selected from the group consisting of serine, threonine, asparagine, aspartic acid, glutamine, glutamic acid, proline, phenyl alanine, lysine, and histidine is below the limit of detection and preferably when the content of all of these free amino acids is below the limit of detection, the solid sugar becomes characterized in that the hygroscopicity is significantly low.

The sugar liquid or solid sugar obtained by the method of producing a sugar liquid can be used as fermentation raw materials to culture a microorganism to convert sugars into chemical substances, thereby producing the chemical substance. Specific examples of the chemical substance can include substances produced in a large scale in the fermentation industry such as alcohols, organic acids, amino acids, or nucleic acids. Examples can include alcohols such as ethanol, 1,3-propanediol, 1,4-butanediol, or glycerol; organic acids such as acetic acid, lactic acid, pyruvic acid, succinic acid, malic acid, itaconic acid, or citric acid; nucleosides such as inosine or guanosine, nucleotides such as inosinic acid or guanylic acid, and amine compounds such as cadaverine. Further, the sugar liquid or solid sugar can also be applied to production of enzymes, antibiotics, recombinant proteins, or the like.

When the obtained sugar liquid is used in fermentation raw materials for production of chemical substances, nitrogen sources and inorganic salts, as necessary, and organic trace nutrients such as amino acids or vitamins, as necessary, may be contained as appropriate. Further, in some cases, besides xylose, sugars such as glucose, sucrose, fructose, galactose, or lactose, starch syrup liquid containing those sugars, sweet potato molasses, sugar beet molasses, high test molasses, organic acids such as acetic acid, alcohols such as ethanol, glycerin, or the like may be added as carbon sources to be used as the fermentation raw material. As for the nitrogen source, used are ammonia gas, aqueous ammonia, ammonium salts, urea, nitrates, and other organic nitrogen sources which are supplementarily used such as oilcakes, soybean-hydrolyzed liquid, casein digests, other amino acids, vitamins, corn steep liquor, yeast or yeast extracts, meat extract, peptides such as peptone, various fermentation bacterial cells and hydrolysates thereof, or the like. As for the inorganic salt, phosphates, magnesium salts, calcium salts, iron salts, manganese salts, or the like can be added as appropriate.

As for a method of culturing a microorganism, a known fermentation culture method such as batch culture, fed-batch culture, or continuous culture can be employed. In particular, the sugar liquid and/or the concentrated sugar liquid are characterized in that solids are completely removed by an ultrafiltration membrane or the like; and the microorganism used in fermentation can be separated and collected by a technique such as centrifugation or membrane separation to be reused. As for such separation collection and reuse of the microorganism, the microorganism may continuously be separated and collected with a fresh sugar liquid and/or concentrated sugar liquid being added during a period of culturing; or the microorganism may be separated and collected after the end of culturing to reuse in a next batch culture.

EXAMPLES

By way of example, our methods will now be specifically described below. This disclosure is, however, not limited thereto.

Reference Example 1: Measurement of the Concentration of Sugars

The concentration of glucose and xylose contained in a sugar liquid was quantified in HPLC conditions described below by comparing to a standard sample.
Column: Luna $NH_2$ (manufactured by Phenomenex)
Mobile phase: Milli-Q:acetonitrile=25:75 (flow rate 0.6 mL/min)
Reaction solution: none
Detection method: RI (differential refractive index)
Temperature: 30° C.

Reference Example 2: Method of Analyzing Fermentation Inhibitors

Aromatic compounds and furan-based compounds contained in a hydrolysate were quantified in HPLC conditions described below by comparing to a standard sample. Each of the analysis samples was centrifuged at 3500 G for 10 minutes and components in the supernatant were subjected to the analysis below.
Column: Synergi HidroRP 4.6 mm×250 mm (manufactured by Phenomenex)
Mobile phase: acetonitrile—0.1% $H_3PO_4$ (flow rate 1.0 mL/min)
Detection method: UV (283 nm)
Temperature: 40° C.

Acetic acid and formic acid were quantified in the HPLC condition shown below by comparing with a standard sample. Each of the analysis samples was centrifuged at 3500 G for 10 minutes and components in the supernatant were subjected to the analysis below.
Column: Shim-Pack and Shim-Pack SCR101H (manufactured by Shimadzu Corporation) in series
Mobile phase: 5 mM p-toluenesulfonic acid (flow rate 0.8 mL/min)
Reaction solution: 5 mM p-toluenesulfonic acid, 20 mM bis tris, 0.1 mM EDTA.2Na (flow rate 0.8 mL/min)
Detection method: electrical conductivity
Temperature: 45° C.

Reference Example 3: Preparation of Cellulase Derived from *Trichoderma*

Cellulase derived from *Trichoderma* was prepared by the following method.
Preculture
Distilled water was added to corn steep liquor 5% (w/vol), glucose 2% (w/vol), ammonium tartrate 0.37% (w/vol), ammonium sulfate 0.14 (w/vol), potassium dihydrogen phosphate 0.2% (w/vol), calcium chloride dihydrate 0.03% (w/vol), magnesium sulfate heptahydrate 0.03% (w/vol), zinc chloride 0.02% (w/vol), iron chloride (III) hexahydrate 0.01% (w/vol), copper sulfate (II) pentahydrate 0.004% (w/vol), manganese chloride tetrahydrate 0.0008% (w/vol), boric acid 0.0006% (w/vol), and hexaammonium heptamolybdate tetrahydrate 0.0026% (w/vol) such that each indicated concentration was attained; and 100 mL of the resulting mixture was placed in a 500 mL-erlenmeyer flask with baffles followed by autoclave sterilization at 121° C. for 15 minutes. After cooling, the resultant was added with each of PE-M and Tween 80 at 0.01% (w/vol), which PE-M and Tween 80 were, separately from the above mixture, sterilized in an autoclave at 121° C. for 15 minutes. To this preculture medium, *Trichoderma reesei* PC3-7 was inoculated to be $1\times10^5$ microbial cells/mL and cultured at 28° C. for 72 hours, with shaking at 180 rpm to be used as preculture (shaker: BIO-SHAKER BR-40LF manufactured by TAITEC Corporation).

Main Culture

Distilled water was added to corn steep liquor 5% (w/vol), glucose 2% (w/vol), cellulose (Avicel) 10% (w/vol), ammonium tartrate 0.37% (w/vol), ammonium sulfate 0.14% (w/vol), potassium dihydrogen phosphate 0.2% (w/vol), calcium chloride dihydrate 0.03% (w/vol), magnesium sulfate heptahydrate 0.03% (w/vol), zinc chloride 0.02% (w/vol), iron chloride (III) hexahydrate 0.01% (w/vol), copper sulfate (II) pentahydrate 0.004% (w/vol), manganese chloride tetrahydrate 0.0008% (w/vol), boric acid 0.0006% (w/vol), and hexaammonium heptamolybdate tetrahydrate 0.0026% (w/vol) such that each indicated concentration was attained; and 2.5 L of the resulting mixture was placed in a 5 L-stirring jar (DPC-2A manufactured by ABLE Corporation) vessel followed by autoclave sterilization at 121° C. for 15 minutes. After cooling, the resultant was added with each of PE-M and Tween 80 at 0.1%, which PE-M and Tween 80 were, separately from the above mixture, sterilized in an autoclave at 121° C. for 15 minutes; and 250 mL of *Trichoderma reesei* PC3-7 that was in advance precultured in the liquid medium by the above-mentioned method was inoculated. Thereafter, the culture was carried out at 28° C. for 87 hours at 300 rpm and with a aeration rate of 1 vvm; and the resultant was centrifuged and then the supernatant was subjected to membrane filtration (STERICUP-GV manufactured by Millipore, material: PVDF). To the culture medium prepared by the above-mentioned condition, 1/100 volume in terms of protein weight ratio of β-glucosidase (Novozyme 188) was added; and this was used, as cellulase derived from *Trichoderma*, in the examples below.

Example 1: Preparation of Cellulose-Containing Biomass Pretreatment Product

1. Preparation of Cellulose-Containing Biomass Pretreatment Product 1 (Ammonia Treatment)

Rice straw was used as cellulose-containing biomass. The rice straw was fed in a small-sized reactor (manufactured by Taiatsu Techno Corporation, TVS-N2 30 ml) and cooled with liquid nitrogen. Ammonia gas was flowed into this reactor and samples were completely immersed in liquid ammonia. The lid of the reactor was closed; and the sample was left to stand at room temperature for about 15 minutes. The treatment was carried out in an oil bath at 150° C. for one hour. After the treatment, the reactor was taken out from the oil bath; and the ammonia gas was immediately discharged in a fume hood and then the inside of the reactor was evacuated to 10 Pa using a vacuum pump to allow the sample to be dried. This was used the following examples as biomass pretreatment product 1.

2. Preparation of Cellulose-Containing Biomass Pretreatment Product 2 (Hydrothermal Treatment)

Rice straw was used as cellulose-containing biomass. The rice straw was immersed in water and subjected, while stirred, to treatment with an autoclave (manufactured by Nitto Koatsu) at 210° C. for 20 minutes. After the treatment, the resultant was subjected to solid-liquid separation through centrifugation (3000 G), separating into a solution component (hereinafter, hydrothermal treatment liquid) and a biomass treatment component. The obtained hydrothermal treatment liquid was used the following examples as biomass pretreatment product 2.

Example 2: Hydrolysis of Cellulose-Containing Biomass (Each of the Pretreatment Products of Example 1)

To the biomass pretreatment product 1 (0.5 g) prepared in Example 1, distilled water was added and then 0.5 mL of cellulase derived from *Trichoderma* prepared in Reference Example 3 was added thereto. Distilled water was further added thereto such that the total weight was 10 g and the pH was adjusted to a range of 4.5 to 5.3 with diluted sulfuric acid or diluted sodium hydroxide. In addition, to 10 g of the hydrothermal treatment liquid adjusted in Example 1, 0.1 mL of cellulase derived from *Trichoderma* prepared in Reference Example 3 was added. The total weight was adjusted to be 10.1 g and the pH was adjusted to a range of 4.5 to 5.3 with diluted sulfuric acid or diluted sodium hydroxide.

The above two types of the compositions whose pH had been adjusted were transferred to a test tube with branch mouth (manufactured by Tokyo Rikakikai Co., Ltd., φ30 NS14/23); and this composition was transferred to a reaction vessel with branch (manufactured by Tokyo Rikakikai Co., Ltd., φ30 NS14/23). With the temperature being kept at 50° C. for 24 hours, the composition, while stirred, underwent hydrolysis (manufactured by Tokyo Rikakikai Co., Ltd.: small-sized mechanical stirrer CPS-1000, a conversion adaptor, an addition port with three-way stopcock, a thermal insulation apparatus MG-2200). The hydrolysate was subjected to solid-liquid separation through centrifugation (3000 G, 10 minutes) to separate a solution component (6 mL) and a solid. The obtained solution component was further filtered with a microfiltration membrane (syringe filter manufactured by General Electric Company); and the obtained filtrate was designated as hydrolysate 1 (from the biomass pretreatment product 1) and hydrolysate 2 (from the biomass pretreatment product 2).

In addition, hydrolysis of biomass by dilute sulfuric acid treatment was carried out. Corncob was used as the biomass and immersed in sulfuric acid water (0.5% by weight) and subjected, while stirred, to treatment with an autoclave (manufactured by Nitto Kouatsu) at 180° C. for 10 minutes. After the treatment, the resultant was subjected to solid-liquid separation through centrifugation (3000 G), separating into a solution component (hereinafter referred to as dilute sulfuric acid treated liquid) and a biomass treatment component. This dilute sulfuric acid treated liquid was further filtered with a microfiltration membrane (syringe filter manufactured by General Electric Company); and the obtained filtrate was designated as hydrolysate 3.

The concentration of sugars (the concentration of glucose and the concentration of xylose) and the concentration of fermentation inhibitors in the above-mentioned hydrolysates 1 to 3 were measured by the methods described in Reference Example 1 and Reference Example 2. A hydrolysate obtained from the biomass pretreatment 1 was designated as hydrolysate 1 and a hydrolysate from the hydrothermal treatment liquid was as hydrolysate 2, both of which were used in the following examples. Further, the results of analysis of sugars and analysis of aromatic compounds for the hydrolysates 1 to 3 are summarized in Table 1.

TABLE 1

|  | Hydrolysate 1 | Hydrolysate 2 | Hydrolysate 3 |
|---|---|---|---|
| Glucose (g/L) | 17.5 | 5 | 4 |
| Xylose (g/L) | 11.0 | 14 | 11 |
| Furfural (mg/L) | 2 | 600 | 452 |
| Hydroxymethylfurfural (mg/L) | 1.5 | 120 | 98 |
| Vanillin (mg/L) | 90 | 12 | 13 |
| Ferulic acid (mg/L) | 0.6 | 2 | 0 |
| Ferulamide (mg/L) | 320 | 0 | 0 |
| Coumaric acid (mg/L) | 0 | 0 | 0 |
| Coumaramide (mg/L) | 120 | 0 | 0 |

We confirmed in the analysis of aromatic compounds on the hydrolysates 1 to 3 that all of the hydrolysates contained one or more types of fermentation inhibitors selected from the group consisting of coumaric acid, coumaramide, ferulic acid, ferulamide, vanillin, vanillic acid, acetovanillone, furfural, and 3-hydroxymethylfurfural, although the type of components contained or the concentration thereof were different.

Example 3: Decomposition of Fermentation Inhibitors by a Microorganism Incapable of Utilizing Glucose and/or Xylose 1. Test Bacterium and Preculture As the microorganism incapable of utilizing glucose and/or xylose, *Delftia* microorganisms (*Delftia acidovorans* NBRC14950, *Delftia tsuruhatensis* NBRC16741) were used. The test bacterium was each cultured in TB medium (pH 7) with shaking for 24 hours. After the culturing, bacterial cells were collected by centrifugation.

2. Fermentation Inhibitor Decomposition Treatment

The hydrolysate 1, hydrolysate 2 and hydrolysate 3 obtained in Example 2 were adjusted to pH 7 and the above-mentioned precultured bacterial cells were added thereto to be $O.D._{600}=10$. The temperature was kept at 30° C. for 24 hours. Thereafter, the obtained sugar liquid was centrifuged (15,000 rpm, 10 min); and the concentration of sugars and the concentration of fermentation inhibitors in the obtained sugar liquid supernatant were measured. The measurement results are shown in Tables 2 and 3. A sugar liquid obtained by subjecting the hydrolysate 1, the hydrolysate 2, and the hydrolysate 3 to the decomposition treatment using *Delftia acidovorans* were used as "sugar liquid 1DA," "sugar liquid 2DA," and "sugar liquid 3DA" in the example described later, respectively. In addition, a sugar liquid obtained by subjecting the hydrolysate 1, the hydrolysate 2, and the hydrolysate 3 to the decomposition treatment using *Delftia tsuruhatensis* was designated as "sugar liquid 1DT," "sugar liquid 2DT," and "sugar liquid 3DT," respectively.

TABLE 2

Fermentation inhibitor decomposition treatment by *Delftia acidovorans*

|  | Sugar liquid 1DA | Sugar liquid 2DA | Sugar liquid 3DA |
|---|---|---|---|
| Glucose (g/L) | 17.5 | 5 | 4 |
| Xylose (g/L) | 11.0 | 14 | 11 |
| Furfural (mg/L) | 0 | 14 | 20 |
| Hydroxymethylfurfural (mg/L) | 0 | 18 | 16 |
| Vanillin (mg/L) | 0 | 2 | 9 |
| Ferulic acid (mg/L) | 0 | 0 | 0 |
| Ferulamide (mg/L) | 5 | 0 | 0 |
| Coumaric acid (mg/L) | 0 | 0 | 0 |
| Coumaramide (mg/L) | 10 | 0 | 0 |

TABLE 3

Fermentation inhibitor decomposition treatment by *Delftia tsuruhatensis*

|  | Sugar liquid 1DT | Sugar liquid 2DT | Sugar liquid 3DT |
|---|---|---|---|
| Glucose (g/L) | 17.5 | 5 | 4 |
| Xylose (g/L) | 11.0 | 14 | 11 |
| Furfural (mg/L) | 0 | 14 | 20 |
| Hydroxymethylfurfural (mg/L) | 0 | 18 | 13 |
| Vanillin (mg/L) | 0 | 2 | 9 |
| Ferulic acid (mg/L) | 0 | 0 | 0 |
| Ferulamide (mg/L) | 5 | 0 | 0 |
| Coumaric acid (mg/L) | 0 | 0 | 0 |
| Coumaramide (mg/L) | 10 | 0 | 0 |

As shown in Tables 2 and 3, we confirmed that the amounts of furfural, hydroxymethylfurfural, vanillin, coumaric acid, coumaramide, ferulamide, and ferulic acid, which are fermentation inhibitors, were reduced by the *Delftia* microorganism. On the other hand, we confirmed that the amounts of glucose and xylose in the sugar liquid did not decrease.

Comparative Example 1: Comparison to a Microorganism that is Capable of Utilizing Glucose and Xylose As microorganisms capable of utilizing glucose and xylose, *Escherichia coli* JM109 strain (Takara Bio Inc.) and wine yeast OC2 strain were used. Each of the test bacteria was cultured in LB medium (pH 7) with shaking for 24 hours. After cultured for 24 hours, bacterial cells were collected by centrifugation.

To the hydrolysate 1, hydrolysate 2 and hydrolysate 3 obtained in Example 2 and Example 3, the above-mentioned precultured bacterial cells were added to be $O.D._{600}=10$. The temperature was kept at 30° C. for 24 hours. Thereafter, the obtained sugar liquid was centrifuged (15,000 rpm, 10 min); and the concentration of sugars and the concentration of fermentation inhibitors in the obtained sugar liquid supernatant were measured. The measurement results are shown in Tables 4 and 5.

TABLE 4

*Escherichia coli* (JM109 strain)

|  | Hydrolysate 1 | Hydrolysate 2 | Hydrolysate 3 |
|---|---|---|---|
| Glucose (g/L) | 6.4 | 2 | 1 |
| Xylose (g/L) | 10.0 | 13 | 9 |
| Furfural (mg/L) | 2 | 560 | 422 |
| Hydroxymethylfurfural (mg/L) | 1.5 | 111 | 93 |
| Vanillin (mg/L) | 88 | 10 | 10 |
| Ferulic acid (mg/L) | 0.6 | 2 | 0 |
| Ferulamide (mg/L) | 318 | 0 | 0 |
| Coumaric acid (mg/L) | 0 | 0 | 0 |
| Coumaramide (mg/L) | 121 | 0 | 0 |

TABLE 5

*Saccharomyces cerevisiae* (OC2 strain)

|  | Hydrolysate 1 | Hydrolysate 2 | Hydrolysate 3 |
|---|---|---|---|
| Glucose (g/L) | 1 | 0 | 0 |
| Xylose (g/L) | 11.0 | 14 | 11 |
| Furfural (mg/L) | 0 | 224 | 148 |
| Hydroxymethylfurfural (mg/L) | 0 | 58 | 32 |

TABLE 5-continued

| Saccharomyces cerevisiae (OC2 strain) | | | |
| --- | --- | --- | --- |
| | Hydrolysate 1 | Hydrolysate 2 | Hydrolysate 3 |
| Vanillin (mg/L) | 88 | 11 | 10 |
| Ferulic acid (mg/L) | 0.3 | 1 | 0 |
| Ferulamide (mg/L) | 298 | 0 | 0 |
| Coumaric acid (mg/L) | 0 | 0 | 0 |
| Coumaramide (mg/L) | 117 | 0 | 0 |

When *Escherichia coli* was used, we confirmed that most of the aromatic compounds did not decrease. In addition, in wine yeast, the amounts of furfural and hydroxymethylfurfural were confirmed to slightly decrease whereas the amounts of coumaramide, coumaric acid, ferulic acid, ferulamide, and vanillin were proven to barely decrease. Further, we confirmed that the amounts of glucose and xylose contained in the hydrolysates 1 to 3 decreased significantly.

Example 4: Ethanol Fermentation Test

Fermentation of ethanol, which was one type of chemical substances, was evaluated by using the sugar liquid obtained in Example 3. *Escherichia coli* KO11 strain (ATCC55124 strain) was precultured in LB medium (2 mL) at 30° C. for 24 h in a test tube. For the sugar liquid 1DA, the sugar liquid 2DA, the sugar liquid 3DA, the sugar liquid 1DT, the sugar liquid 2DT, and the sugar liquid 3DT, a fermentation medium (2 mL) was prepared with yeast extract (5 g/L), peptone (10 g/L), and sodium chloride (5 g/L), and with the pH being adjusted to 7.0. To each fermentation medium, 100 μL of the preculture liquid which was precultured as described above was added and cultured at 30° C. for 24 hours. After 24-hour culturing, the cumulative concentration of ethanol generated in each sugar liquid was measured by gas chromatography (Shimadzu GC-2010 capillary GC TC-1 (GL science) 15 meter L. *0.53 mm I.D., df1.5 μm was used and a flame ionization detector was used for detection and calculation for evaluation).

TABLE 6

| | Sugar liquid 1DA | Sugar liquid 2DA | Sugar liquid 3DA |
| --- | --- | --- | --- |
| Amount of EtOH produced (g/L) | 14.2 | 10.6 | 6.8 |

| | Sugar liquid 1DT | Sugar liquid 2DT | Sugar liquid 3DT |
| --- | --- | --- | --- |
| Amount of EtOH produced (g/L) | 14.6 | 10.2 | 6.2 |

Comparative Example 2: Ethanol Fermentation Test

Fermentation of ethanol, which was one type of chemical substances, was evaluated by using the hydrolysates 1 to 3 obtained in Example 2.

TABLE 7

| | Hydrolysate 1 | Hydrolysate 2 | Hydrolysate 3 |
| --- | --- | --- | --- |
| Amount of EtOH produced (g/L) | 7.2 | 1.3 | 1.5 |

In comparison of the result of the ethanol fermentation in Example 4 (Table 6) with the result of the ethanol fermentation in Comparative Example 2 (Table 7), reduction of the fermentation inhibitors in the step (2) resulted in a significantly higher amount of ethanol produced in the ethanol fermentation in Example 4.

Example 5: Metabolic Decomposition of Ferulamide and Ferulic Acid by *Delftia* Microorganisms To check whether or not the decomposition of aromatic compounds in the hydrolysate of Example 3 is caused by *Delftia* microorganism, a model reaction system with ferulamide being added was employed to identify decomposition products and to track a change in the amount generated.

Figure 3:
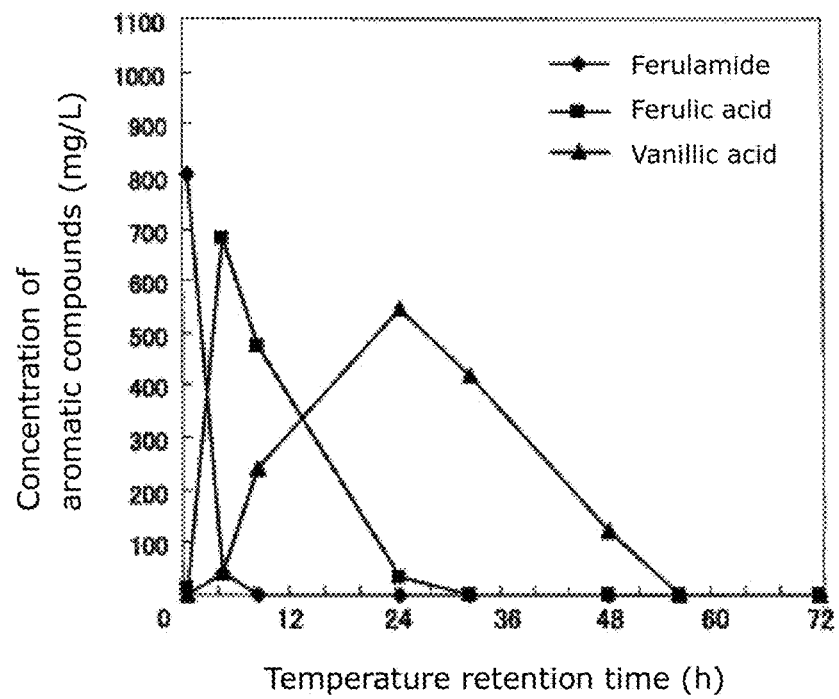
FIG. 3 is a drawing showing a change in ferulamide by *Delftia tsuruhatensis*, the change being tracked over time.
Figure 4:
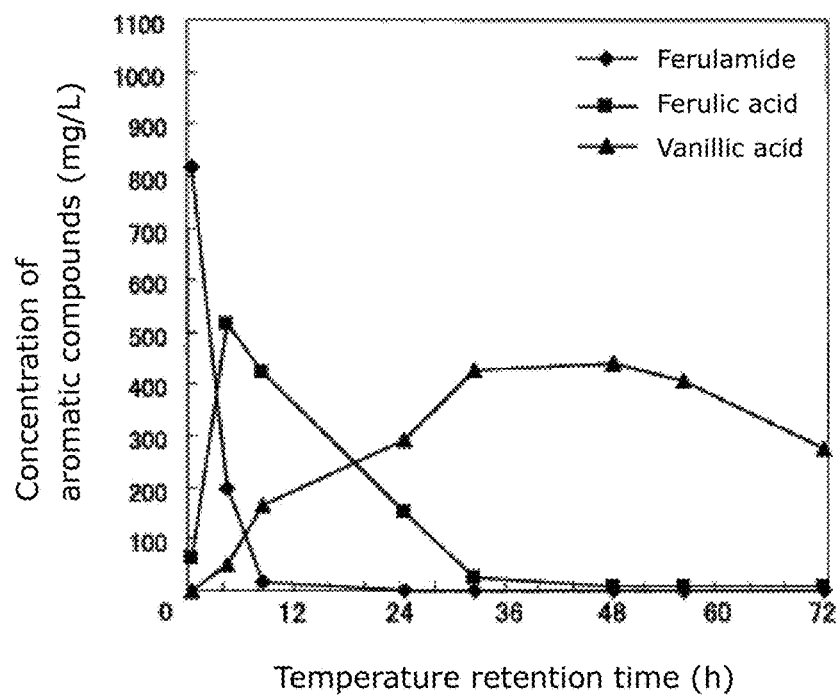
FIG. 4 is a drawing showing a change in ferulamide by *Delftia acidovorans*, the change being tracked over time.

*Delftia acidovorans* NBRC14950 and *Delftia tsuruhatensis* NBRC16741 were cultured with shaking in TB medium (pH 7) for 64 hours. After the culturing, cells of each of the bacteria were collected by centrifugation. A solution prepared by dissolving ferulamide in N,N-dimethylformamide was diluted with a 10 mM Tris-HCl buffer to prepare a 1 g/L ferulamide solution and the pH was adjusted to 10 with sodium hydroxide. The above-mentioned cells of each bacterium that had been previously collected were added to attain $O.D._{600}=10$. The temperature was kept at 30° C. for 72 hours and the reaction solution was collected with time. The obtained reaction solution was centrifuged (15,000 rpm, 10 min) and the concentration of aromatic compounds in the obtained reaction solution supernatant was measured by the method in Reference Example 1. The results of *Delftia tsuruhatensis* are shown in FIG. 3 and the results of *Delftia acidovorans* are shown in FIG. 4. As shown in FIGS. 3 and 4, in both bacteria of the genus *Delftia*, the concentration of ferulamide sharply decreased soon after the start of temperature retention and the amount of ferulic acid generated peaked six hours later. Further, we confirmed that the ferulic acid disappeared within 36 hours after that peak and converted into vanillic acid. Further, the vanillic acid was confirmed to further decrease over a time period of temperature retention. From the above results, we confirmed that the compound was converted into, in sequence, ferulamide, ferulic acid, and vanillic acid in the *Delftia* microorganism, and the vanillic acid was eventually decomposed as well.

Example 6: Metabolic Decomposition of Coumaramide and Coumaric Acid by *Delftia* Microorganisms To check whether or not the decomposition of aromatic compounds in the hydrolysate of Example 3 is caused by the *Delftia* microorganism, a model reaction system with coumaramide being added was employed to identify decomposition products and to track a change in the amount generated.

Figure 5:
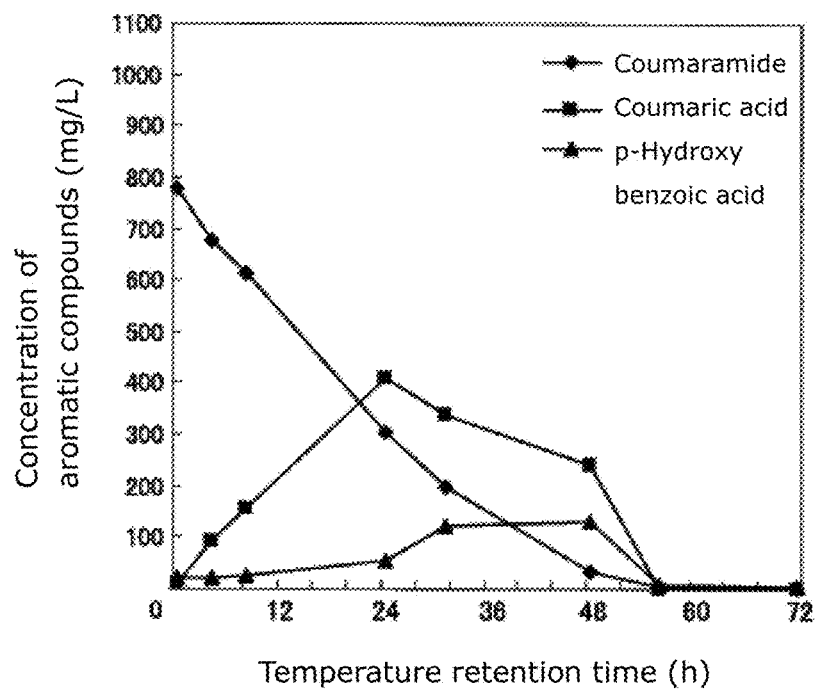
FIG. 5 is a drawing showing a change in coumaramide by *Delftia tsuruhatensis*, the change being tracked over time.
Figure 6:
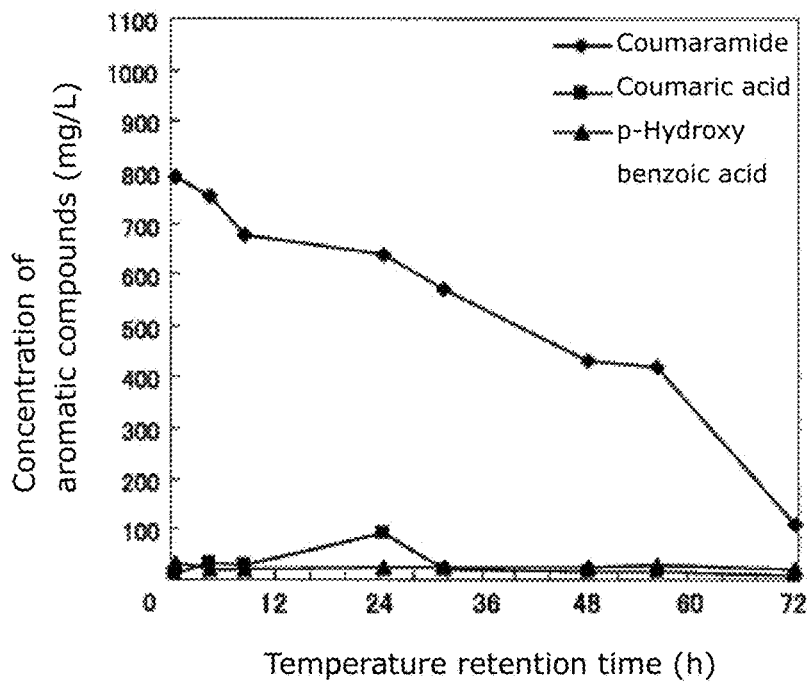
FIG. 6 is a drawing showing a change in coumaramide by *Delftia acidovorans*, the change being tracked over time.

The identification of metabolic pathway was carried out in the same procedures as described in Example 5 except that ferulamide was changed to coumaramide. The results of *Delftia tsuruhatensis* are shown in FIG. 5 and the results of *Delftia acidovorans* are shown in FIG. 6. As shown in FIGS. 5 and 6, it became clear that, in both bacteria of the genus *Delftia*, the concentration of coumaramide gradually decreased over 48 hours or more from the beginning of the temperature retention. In addition, the concentration of coumaric acid became increased as the coumaramide decreased and peaked 24 hours after the beginning of the temperature retention. Further, as shown in FIG. 5, we confirmed that p-hydroxybenzoic acid was generated as the coumaric acid decreased in *Delftia tsuruhatensis*. Similarly, generation of p-hydroxybenzoic acid was, albeit in a small amount, confirmed also in *Delftia acidovorans*. From the above results, we confirmed that the compound was converted into, in sequence, coumaramide, coumaric acid, and p-hydroxybenzoic acid in the *Delftia* microorganism, and the p-hydroxybenzoic acid was eventually decomposed as well.

Example 7: Effect of pH on Decomposition of Fermentation Inhibitors by *Delftia* Microorganisms The hydrolysate 1 of Example 2 was adjusted to have pH 4, pH 8.5, pH 10, or pH 12; and the decomposition treatment of fermentation inhibitors was carried out in the same procedures as described in Example 4. *Delftia tsuruhatensis* was used as a test bacterium. The results are shown in Table 8.

TABLE 8

| | pH 7 (Example 3) | pH 5 | pH 8 | pH 10 | pH 12 |
|---|---|---|---|---|---|
| Glucose (g/L) | 17.5 | 17.0 | 17.5 | 17.5 | 17.5 |
| Xylose (g/L) | 11.0 | 11.0 | 11.0 | 11.0 | 11.0 |
| Furfural (mg/L) | 0 | 1 | 0 | 0 | 2 |
| Hydroxymethylfurfural (mg/L) | 0 | 1.0 | 0 | 0 | 1.2 |
| Vanillin (mg/L) | 0 | 56 | 0 | 0 | 89 |
| Ferulic acid (mg/L) | 0 | 0.4 | 0 | 0 | 18 |
| Ferulamide (mg/L) | 5 | 220 | 2 | 0 | 320 |
| Coumaric acid (mg/L) | 0 | 0 | 0 | 0 | 6 |
| Coumaramide (mg/L) | 10 | 80 | 5 | 0 | 100 |

We confirmed a small decrease in the aromatic compound at pH 5 and pH 12. On the other hand, we confirmed that the amount of the aromatic compound decreased more at pH 8 and pH 10 than at pH 7 (Example 3) and, in particular, coumaramide and ferulamide were confirmed to significantly decrease. As shown in Reference Example 5, the *Delftia* microorganism was confirmed not to grow at pH 10; and it was thus presumed that, although the *Delftia* microorganism did not proliferate at pH 10, aromatic compound converting enzymes possessed by the *Delftia* microorganism were functioning to progress the decomposition of the aromatic compound.

Reference Example 4: Optimum Growth Temperature of *Delftia* Microorganisms

The optimum growth temperature of the genus *Delftia* was investigated. *Delftia tsuruhatensis* of Example 3 was used as a test bacterium; and the bacterium was precultured in LB medium (5 mL) at 30° C. and 180 rpm for 24 hours in a test tube. Thereafter, 50 μL of the preculture liquid that was precultured as described above was added to TB medium (5 mL, pH 7) and cultured at 30° C. to 50° C. and 180 rpm for 24 hours. After 24-hour culturing, $OD_{600}$ was measured. The results are shown in Table 9.

TABLE 9

| | 20° C. | 30° C. | 35° C. | 40° C. | 50° C. |
|---|---|---|---|---|---|
| $OD_{600}$ | 6.4 | 9.7 | 4.8 | 0.08 | 0.03 |

We confirmed that the microorganism proliferated in a temperature range of 20° C. to 35° C. The microorganism was, however, confirmed not to proliferate above 40° C.

Reference Example 5: Optimum Growth pH of *Delftia* Microorganisms

The optimum growth pH of *Delftia* microorganisms was investigated. *Delftia tsuruhatensis* was used as a test bacterium and the bacterium precultured in LB medium (5 mL) at 30° C. and 180 rpm for 24 hours in a test tube. Thereafter, 50 μL of the preculture liquid that was precultured as described above was added to each of TB media whose pH was adjusted to 4.0, 8.5, and 10 using TB medium (5 mL, pH 7), hydrochloric acid, and sodium hydroxide, and cultured at 30° C. and 180 rpm for 24 hours. After 24-hour culturing, $OD_{600}$ was measured. The results are shown in Table 10.

TABLE 10

| | pH 4.0 | pH 7.0 (Reference Example 3) | pH 8.5 | pH 10 |
|---|---|---|---|---|
| $OD_{600}$ | 0 | 9.7 | 8.8 | 0 |

We confirmed that the genus *Delftia* proliferated up to pH 8.5 and did not grow at all at pH 10. Further, similarly at pH 4, no proliferation was confirmed.

Example 8: Step of Subjecting Sugar Liquid to Membrane Concentration (Reverse Osmosis Membrane)

For the sugar liquid 1DA, the sugar liquid 2DA, and the sugar liquid 3DA which were described in Example 3, 1300 mL of each was subjected to a microfiltration membrane having a pore diameter of 0.22 μm (STERICUP-GV, manufactured by Millipore) to remove fine particles contained. The obtained liquid was filtered at 30° C. using reverse osmosis membrane (UTC-80, manufactured by Toray Industries, Inc.) in a flat sheet membrane small-sized cross flow filtration unit (SEPA CF-II, manufactured by GE Osmonics, effective membrane area 140 cm$^2$). The filtration was carried out while a transmembrane pressure difference in the cross flow filtration adjusted whenever necessary to be 4 MPa at all times; and the membrane concentration was carried out until the liquid volume became to about 1/4 (four-fold concentration). A time required for the concentration, a filtration rate at the end of the concentration, and the concentration of sugars after the concentration were measured. The results are shown in Table 8. Further, as a comparative example (Comparative Example 3), hydrolysates 1 to 3 described in Example 3 (for which the step of decomposing fermentation inhibitors by a microorganism incapable of utilizing glucose and xylose was not carried out) were used to carry out the membrane concentration in the same procedures as described above by the above-mentioned method. The results are shown in Table 11.

TABLE 11

| | Sugar liquid | Time required for concentration (min) | Filtration rate at the end of concentration (m$^3$/m$^2$/day) | Sugar concentration after concentration (g/L) | |
|---|---|---|---|---|---|
| | | | | Glucose | Xylose |
| Example 8 | Sugar liquid 1DA | 125 | 0.32 | 68.6 | 44.4 |
| | Sugar liquid 2DA | 105 | 0.55 | 19.4 | 56.9 |
| | Sugar liquid 3DA | 93 | 0.58 | 16.7 | 43.5 |

TABLE 11-continued

| | Sugar liquid | Time required for concentration (min) | Filtration rate at the end of concentration (m³/m²/day) | Sugar concentration after concentration (g/L) | |
|---|---|---|---|---|---|
| | | | | Glucose | Xylose |
| Compar- | Hydrolysate 1 | 160 | 0.19 | 68.5 | 43.9 |
| ative | Hydrolysate 2 | 144 | 0.25 | 20.0 | 56.0 |
| Example 3 | Hydrolysate 3 | 138 | 0.25 | 17.2 | 43.5 |

As shown in Table 11, the time required for the four-fold concentration of the sugar liquid was shortened more in the sugar liquid for which the step of decomposing fermentation inhibitors by a microorganism incapable of utilizing glucose and xylose was carried out. Further, the filtration rate at the end of the concentration was larger when the step of decomposing the fermentation inhibitor by a microorganism incapable of utilizing glucose and xylose was carried out. From these, it was became clear that the filterability at the time of membrane concentration of the sugar liquid was improved by subjecting each of the hydrolysates to the step of decomposing fermentation inhibitors by a microorganism incapable of utilizing glucose and xylose.

Example 9: Preparation of Solid Sugar

For the sugar liquid 1DA after the membrane concentration described in Example 8 and, for the sake of comparison, the hydrolysate 1 after the membrane concentration described in the same Example 8, those were each aliquoted into 15 mL, transferred to a glass round-bottomed flask, and frozen at −70° C. The above-mentioned frozen sugar liquid and hydrolysate 1 were subjected to freeze drying in a lyophilizer (EYELA: Tokyo Rikakikai Co., Ltd.) that was set at −45° C. for 48 hours. The weight after the drying of the sugar liquid 1DA after the membrane concentration was 1.41 g and that of the hydrolysate 1 was 1.37 g.

Figure 7:
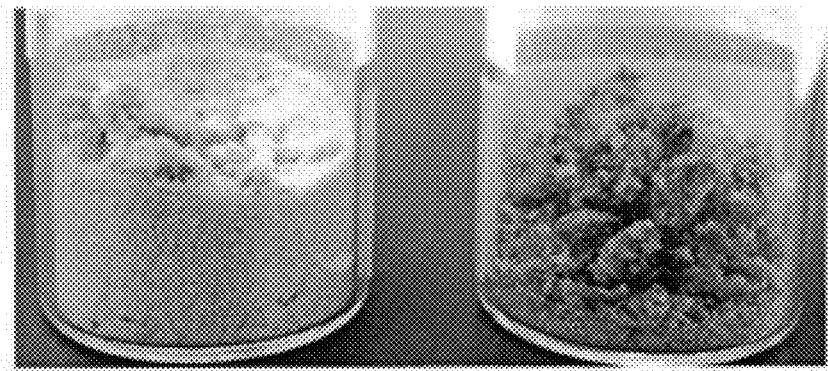
FIG. 7 is a photograph showing a change in the solid sugar, the change being tracked over time.
Figure 7:
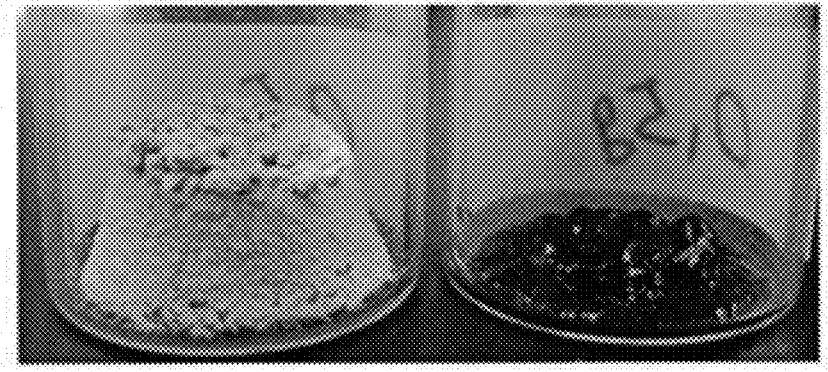

To a glass vial bottle (capacity 13.5 mL), 0.5 g of each of the obtained solid sugar (solid sugar 1DA: one obtained by freeze-drying the sugar liquid 1DA after the membrane concentration) and the solid sugar hydrolysate 1 (one obtained by freeze-drying hydrolysate 1 after the membrane concentration) was collected. Thereafter, those were left to stand with the lid of the vial bottle open at room temperature (about 25° C.) for 24 hours; and changes in the outer appearance were compared. The results were shown in FIG. 7. In the solid sugar hydrolysate 1, moisture absorption begins in the step of aliquoting the freeze-dried product from the round-bottomed flask to the vial bottle, which is shown in clusters with a dark color tone in a photograph immediately after the opening (FIG. 7A right side). On the other hand, the solid sugar 1DA remained as powder (FIG. 7A left side). Thereafter, the lid of the vial bottle was opened. FIG. 7B shows a photograph 24 hours after opening. The solid sugar hydrolysate 1 fully absorbed moisture, was no longer in the form of powder, and turned into viscous molasses (FIG. 7B left side). On the other hand, the solid sugar 1DA exhibited some seemingly decreased bulkiness and thus presumably absorbed moisture, but kept the powder state even after 24 hours, which confirmed a significant difference. That is, the solid sugar had an extremely high form stability in open air due to its low hygroscopicity and we confirmed that the solid sugar was advantageous in practice.

Example 10: Amino Acid Analysis

An analysis of amino acids contained in the solid sugar hydrolysate 1 and the solid sugar 1DA which were obtained in Example 9 was carried out by the following procedure. In the amino acid analysis, the concentration of free amino acids was measured. As for an analytical apparatus, Amino Acid Analyzer L-8800A (Hitachi, Ltd.) was employed and the analysis was carried out in measurement conditions using ninhydrin method and a detection wavelength of 440 nm (proline and hydroxyproline) and 570 nm (amino acids other than proline and hydroxyproline).

From the freeze-dried product, the solid sugar hydrolysate 1 (1.41 g), and the solid sugar 1DA (1.37 g), all of which were obtained in Example 9, 2.05 mg of each was collected to a tube and 250 µL of 2% sulfosalicylic acid was added thereto and stirred, followed by 10-minute ultrasonication. This solution was filtered with 0.22 µm filter and used as a sample solution for measurement. The analysis was carried out using 25 µL of this sample solution in the above-mentioned apparatus conditions. The analysis values are shown in Table 12.

TABLE 12

| | Solid sugar 1DA (Sugar liquid 1DA) | | Solid sugar hydrolysate 1 (Hydrolysate 1) | |
|---|---|---|---|---|
| | Detection concentration (mg/g of solid) | Sugar liquid concentration conversion (mg/L) | Detection concentration (mg/g of solid) | Sugar liquid concentration conversion (mg/L) |
| Aspartic acid | 0.0262 | 2.46 | 0.4947 | 45.18 |
| Threonine | undetectable | 0 | 0.3255 | 29.37 |
| Serine | undetectable | 0 | 0.2976 | 27.18 |
| Asparagine | undetectable | 0 | 0.5193 | 47.43 |
| Glutamic acid | undetectable | 0 | 0.4400 | 40.19 |
| Glutamine | undetectable | 0 | 0.0738 | 6.74 |
| Proline | undetectable | 0 | 0.0983 | 8.98 |
| Glycine | 0.0274 | 2.58 | 0.2164 | 19.76 |
| Alanine | 0.0942 | 8.85 | 0.7362 | 67.24 |
| Valine | 0.0569 | 5.35 | 0.3563 | 32.54 |
| Methionine | 1.2929 | 121.53 | 0.9037 | 82.45 |
| Isoleucine | 0.0121 | 1.14 | 0.5080 | 46.40 |
| Leucine | 0.0381 | 3.58 | 0.5506 | 50.29 |
| Tyrosine | 0.0595 | 5.59 | 0.3720 | 33.98 |
| Phenylalanine | undetectable | 0 | 0.2818 | 25.74 |
| β-alanine | 0.0374 | 3.52 | 0.0392 | 3.58 |
| Lysine | undetectable | 0 | 0.2980 | 27.22 |
| Histidine | undetectable | 0 | 0.0485 | 4.43 |
| Arginine | 0.0619 | 5.82 | 0.5142 | 49.46 |

A detection concentration is the concentration of each of the free amino acids (mg) that is contained in 1 g of the weight of the solid sugar analyzed. A concentration conversion in the concentrated sugar liquid is a value of converted concentration of amino acids present in 15 mL of each membrane-concentrated sugar liquid subjected to freeze drying. We confirmed from the analysis value that all of the amino acids were contained in the solid sugar hydrolysate 1. On the other hand, in the solid sugar 1DA for which the decomposition of fermentation inhibitors by a microorganism incapable of utilizing glucose and xylose was carried out, no free amino acids of serine, threonine, asparagine, aspartic acid, glutamine, glutamic acid, proline, phenyl alanine, lysine, and histidine were able to be detected (undetectable). Therefore, we confirmed that the concentration of free amino acids in the concentrated sugar liquid before the freeze drying was 0 mg/L. That is, we confirmed that the above-mentioned concentration of free amino acids was below the limit of detection in the sugar liquid and the solid sugar.

Subsequently, the analysis was similarly carried out for the total amount of amino acids contained in each solid sugar. With regard to the total amount of amino acids, amino acids present in a state of peptide or polypeptide are, in addition to free amino acids, included as well. Therefore, from the freeze-dried product, the solid sugar hydrolysate 1 (1.41 g), and the solid sugar 1DA (1.37 g), all of which were obtained in Example 9, 2.05 mg of each was collected to a tube; and 250 μL of 6 mol/L hydrochloric acid was added thereto. After nitrogen substitution and tube sealing under reduced pressure, hydrolysis was carried out at 110° C. for 22 hours. This resultant was dried to solidify under reduced pressure to obtain residues, which were added with 200 μL of 0.02 mol/L hydrochloric acid to dissolve. This solution was filtered with a 0.22 μm centrifugal filtration unit and used as a sample solution for measurement. The analysis was carried out using 25 μL of this sample solution in the above-mentioned apparatus conditions. The analysis values are shown in Table 13.

TABLE 13

| | Solid sugar 1DA (Sugar liquid 1DA) | | Solid sugar hydrolysate 1 (Hydrolysate 1) | |
|---|---|---|---|---|
| | Detection concentration (mg/g of solid) | Sugar liquid concentration conversion (mg/L) | Detection concentration (mg/g of solid) | Sugar liquid concentration conversion (mg/L) |
| Aspartic acid | 1.3539 | 127.27 | 2.3565 | 215.23 |
| Threonine | 0.4263 | 40.07 | 0.7123 | 65.06 |
| Serine | 0.3834 | 36.04 | 0.6855 | 62.61 |
| Glutamic acid | 0.9589 | 90.14 | 2.2634 | 206.72 |
| Glycine | 0.7796 | 73.28 | 1.1307 | 103.27 |
| Alanine | 1.1349 | 106.68 | 2.1160 | 193.26 |
| Valine | 0.4775 | 44.89 | 0.8930 | 81.56 |
| Methionine | 0.2826 | 26.56 | 0.6470 | 59.09 |
| Isoleucine | 0.3192 | 30.00 | 0.6749 | 61.64 |
| Leucine | 0.5522 | 51.91 | 1.1997 | 109.57 |
| Tyrosine | 0.2987 | 28.08 | 0.6133 | 56.01 |
| Phenylalanine | 0.3377 | 31.74 | 0.6959 | 63.56 |
| Lysine | 0.3728 | 35.04 | 0.7224 | 65.98 |
| Histidine | 0.1430 | 13.44 | 0.2754 | 25.15 |
| Arginine | 0.3445 | 32.38 | 0.8733 | 79.76 |
| Proline | 0.6074 | 57.10 | 0.7454 | 68.08 |

We confirmed from the analysis values that both of the solid sugar hydrolysate 1 and the solid sugar 1DA for which the decomposition of fermentation inhibitors by a microorganism incapable of utilizing glucose and xylose was carried out contained all of the amino acids. It was however confirmed that the solid sugar 1DA contained less. That is, we confirmed that what was consumed by the microorganism incapable of utilizing glucose and xylose were mainly free amino acids whereas amino acids present in a peptide or polypeptide state were unconsumed and remained in the sugar liquid. It is important in the fermentation production using microorganisms that these amino acids present in a peptide or polypeptide state are contained and the amino acids are used as nitrogen sources for microbial proliferation.

Example 11: Decomposition of Fermentation Inhibitors by a Microorganism Incapable of Utilizing Glucose and/or Xylose (Decomposition 2): Treatment of Blackstrap Molasses (Molasses)

As a sugar aqueous solution containing fermentation inhibitors, blackstrap molasses (molasses: Molasses-Agri, Organic Land Co., Ltd.) was used for preparation. The blackstrap molasses used is a mixture using, as biomass, about 90% of sugarcane-derived blackstrap molasses and about 10% of sweet potato-derived blackstrap molasses. This blackstrap molasses was diluted six-fold with RO water and sterilized in an autoclave at 121° C. for 20 minutes. After sterilization, sodium hydroxide was added and the pH of the resulting mixture was adjusted to 6.7. The resultant was used as a sugar aqueous solution containing fermentation inhibitors (a blackstrap molasses sugar aqueous solution). The analysis results of aromatic compounds are shown in Table 14. We confirmed that the blackstrap molasses sugar aqueous solution contained glucose, fructose and sucrose as the sugar and 3-hydroxymethylfurfural as the fermentation inhibitor. This sugar aqueous solution was subjected to treatment with *Delftia tsuruhatensis* in accordance with what was described in Example 3. The obtained sugar liquid was designated as blackstrap molasses DT; and the analysis values (sugars and aromatic compounds) are shown in Table 14. It was able to be confirmed that 3-hydroxymethylfurfural contained as the fermentation inhibitor was completely decomposed and disappeared from the blackstrap molasses DT.

TABLE 14

| | Blackstrap molasses sugar aqueous solution | Blackstrap molasses DT |
|---|---|---|
| Glucose (g/L) | 53.7 | 53.4 |
| Sucrose (g/L) | 38.8 | 38.8 |
| Fructose (g/L) | 39.9 | 39.5 |
| Hydroxymethylfurfural (mg/L) | 168.5 | 0.0 |
| Vanillin (mg/L) | 0.0 | 0.0 |
| Ferulic acid (mg/L) | 0.0 | 0.0 |
| Ferulamide (mg/L) | 0.0 | 0.0 |
| Coumaric acid (mg/L) | 0.0 | 0.0 |
| Coumaramide (mg/L) | 0.0 | 0.0 |

INDUSTRIAL APPLICABILITY

The method of producing a sugar liquid can be used to produce a sugar liquid with reduced fermentation inhibition from biomass. In addition, the sugar liquid or solid sugar produced can be used as fermentation a raw material for various chemical substances.

The invention claimed is:
1. A method of producing a sugar liquid from biomass, comprising:
  (a) decomposing one or more fermentation inhibitor(s) contained in a sugar aqueous solution obtained from biomass with a microorganism incapable of utilizing glucose and/or xylose or a crude enzyme extract obtained from the microorganism, to obtain a sugar liquid having a reduced fermentation inhibitory activity compared to the sugar aqueous solution; and
  (b) subjecting the sugar liquid obtained in step (a) to membrane concentration and/or evaporation concentration to increase sugar concentration,
  wherein the one or more fermentation inhibitor(s) are selected from the group consisting of coumaric acid, coumaramide, ferulic acid, ferulamide, vanillin, vanillic acid, acetovanillone, furfural, and 3-hydroxymethylfurfural, and the microorganism incapable of utilizing glucose and/or xylose is a *Delftia* microorganism (*Delftia* sp.).

2. The method according to claim 1, wherein the microorganism incapable of utilizing glucose and/or xylose is selected from the group consisting of *Delftia acidovorans, Delftia lacustris, Delftia tsuruhatensis*, and *Delftia litopenaei*.

3. The method according to claim 1, wherein the sugar aqueous solution is a sugar aqueous solution obtained by hydrolyzing cellulose-containing biomass.

4. The method according to claim 3, further comprising preparing the sugar aqueous solution by subjecting the cellulose-containing biomass to one or more treatments selected from the group consisting of an acid treatment, an alkali treatment, a hydrothermal treatment, and an enzyme treatment.

5. The method according to claim 1, wherein the sugar aqueous solution comprises blackstrap molasses.

6. The method according to claim 1, wherein the fermentation inhibitor decomposition treatment is at a monosaccharide concentration of 0.1 g/L to 100 g/L.

7. The method according to claim 1, wherein the fermentation inhibitor decomposition treatment is at a pH of 6 to 11.

* * * * *